(12) United States Patent
Wilson

(10) Patent No.: US 8,133,283 B2
(45) Date of Patent: Mar. 13, 2012

(54) SCAPHO-LUNATE FIXATION IMPLANTS AND METHODS OF USE

(76) Inventor: Kenneth Mitchell Wilson, Oregon City, OR (US)

( * ) Notice: Subject to any disclaimer, the term of this patent is extended or adjusted under 35 U.S.C. 154(b) by 871 days.

(21) Appl. No.: 12/134,899

(22) Filed: Jun. 6, 2008

(65) Prior Publication Data
US 2008/0306480 A1 Dec. 11, 2008

Related U.S. Application Data

(60) Provisional application No. 60/942,306, filed on Jun. 6, 2007.

(51) Int. Cl.
*A61F 2/42* (2006.01)
*A61F 2/46* (2006.01)
(52) U.S. Cl. ........................ 623/21.14; 606/86 R; 606/87
(58) Field of Classification Search .................... 606/62, 606/70, 74, 86 R, 151, 248, 268, 287, 300, 606/87; 623/21.12, 21.13, 21.14, 22.14; 403/167–168, 361
See application file for complete search history.

(56) References Cited

U.S. PATENT DOCUMENTS

| | | | |
|---|---|---|---|
| 5,234,431 A * | 8/1993 | Keller | 606/70 |
| 5,800,436 A * | 9/1998 | Lerch | 606/324 |
| 6,699,292 B2 * | 3/2004 | Ogilvie et al. | 623/21.15 |
| 2003/0078582 A1 * | 4/2003 | Heggeness | 606/69 |

* cited by examiner

*Primary Examiner* — Thomas C. Barrett
*Assistant Examiner* — Christian Sevilla
(74) *Attorney, Agent, or Firm* — Baumgartner Patent Law; Marc Baumgartner

(57) ABSTRACT

Surgical implants for neighboring bones are disclosed herein. Preferred implants are configured to be implanted into the scaphoid and lunate. Preferred implants include a first plate configured to be implanted into the scaphoid and a second plate configured to be implanted into the lunate wherein said first and second plates are couple together by a rotatable rod.

11 Claims, 5 Drawing Sheets

SCAPHO-LUNATE FIXATION IMPLANTS AND METHODS OF USE

CROSS-REFERENCE TO RELATED APPLICATIONS

This application claims priority to U.S. Provisional Application No. 60/942,306, entitled "Scapholunate Interosseus Ligament Enhancement Device" and filed on Jun. 6, 2007, which is expressly incorporated by reference in its entirety.

FIELD OF THE INVENTION

The embodiments herein relate to implant assemblies and methods useful in bone fixation surgeries. More particularly, the teachings herein relate to improving current methods and systems directed to implanting fixation devices in the wrist of a patient in need.

BACKGROUND

Scapholunate Dissociation (SLD) remains one of the most common, and unfortunately, difficult problems to treat in the wrist. SLD generally relates to a tearing or damage to the interosseus ligament that connects the scaphoid and the lunate bones together. This ligament is also known as the scapholunate ligament. SLD often leads to arthritis of the wrist joint characterized with disability and chronic pain. Multiple techniques and implants have been proposed to treat SLD, however the results have been unreliable and disadvantageous.

One prior device for attempting to treat SLD is a rotating screw that is configured to be inserted between the scaphoid and lunate. Each end of the screw is threaded while the body of the screw is smooth to allow for rotation. This configuration unfortunately only allows for a single plane rotation, but not any significant dorsal-volar or radio-ulnar movement that the normal joint possesses. Because the normal scapholunate joint allows for movement in all three planes, this prior art screw does not function as an adequate substitute. As a result of this limited motion design, and the fact that the entire screw is made of metal, the prior art screw tends to pull out of the bone, break after time, or permanently restrict wrist motion.

The above described device and other prior art devices also require the patient to wear a cast or splint for two to three months after the surgery. This long cast time can considerably limit the range of motion in the wrist, and the results can be permanent. Accordingly, an improved, standardized system and approach is needed that is easier for the operating surgeon to implement and has better results and reliability for the patient.

Accordingly, one object of the present invention is to provide more consistent and reliable assemblies and surgical techniques to treat SLD. An additional object is to provide an implant that includes the same, or similar, modulus of elasticity as bone. A further object is to provide implants that allow movement in three different planes (dorsal-volar, radio-ulnar, and rotational movement). Still a further object is to provide a system and method that can treat both acute and chronic cases of SLD in which the dissociation can still be reduced to an anatomical alignment. An additional object of the teachings herein is to provide a device and method that would reduce the time a patient needs to wear a cast after the surgery. A further object of the teachings herein is to provide devices and methods that allow the patient to have early motion between the carpal bones and the radius after the surgery, while still retaining a reliable repair that will improve the final functionality of the wrist.

The above-listed objects of the invention are intended to be non-limiting, as further objects and advantages will be readily appreciated by those with skill in the art upon reading the teachings below.

SUMMARY OF THE INVENTION

According to preferred embodiments, the teachings herein generally relate to a fixation device configured to be implanted into first and second neighboring bones of a patient in need and comprising a first plate having inward and outward facing substantially planar faces and configured to be implanted into the first bone and a second plate having inward and outward facing substantially planar faces and configured to be implanted into the second bone, wherein said inward faces of the first and second plates are coupled together by a lateral rod having first and second ends individually coupled to the first and second plates by means for rotation that allow the rod to rotate between the inward faces of said first and second plates.

According to more specific embodiments, said first and second bones are the scaphoid and lunate. With respect to preferred embodiments, said first plate comprises a first hole and the second plate comprises a second hole laterally aligned with said first hole and wherein said first and second holes comprise a larger perimeter than the cross-section of the rod and wherein said rod's first and second ends are passed through said first and second holes respectively and are individually coupled to first and second anchors on the outward faces of the first and second plates respectively.

Additionally, it is preferred that said first and second anchors are hemispheres in shape, such that the convex face of the hemisphere anchors are positioned toward the outward faces of the first and second plates. Further embodiments provide the outward faces of the first and second plates to individually include a concave area configured to receive the convex faces of the hemisphere anchors. Preferably, said first plate further comprises one or more perforations laterally aligned with one or more perforations on the second plate and wherein the one or more laterally aligned perforations are configured to receive a Kirschner wire.

Advantageously, the means for rotation further allow the rotation of the first and/or second plate around the rod. Further preferred embodiments include said first and second plates comprising pyrocarbon.

Preferred methods of implanting the fixation devices into the scaphoid and lunate of a patient in need include providing a fixation device having a first and second plates connected by a rotatable rod; wherein said first plate is configured to be implanted into the scaphoid and said second plate is configured to be implanted into the lunate, aligning a cutting jig comprising an outline of the fixation device on the dorsal face of the scaphoid and lunate, cutting out a space in the scaphoid and lunate in the shape of the outline, and implanting said fixation device into said scaphoid and lunate such that the first and second plates of the fixation device do not extend out past the cortices of the scaphoid or lunate.

More specific embodiments include methods wherein the cut out space in the scaphoid and lunate allows for rotation of the rod and the plates after implantation. Further preferred methods include a tamp having members configured to push down on the fixation device to implant said fixation device. Preferably said tamp is configured to work with a Kirschner wire jig for alignment of the fixation device.

Further embodiments relate to a surgical kit for implanting a fixation device into the scaphoid and lunate of a patient in need comprising: a fixation device having a first and second plates connected by a rotatable rod; wherein said first plate is configured to be implanted into the scaphoid and said second plate is configured to be implanted into the lunate.

Said surgical kit can further include one or more of the following: a tamp for implanting said fixation device, a Kirschner wire jig for aligning the implant, Kirschner wires for temporarily aligning said fixation device in the scaphoid and lunate, and a cutting jig having an outline of the fixation device and configured to allow a health provider to cut the shape of the fixation device into the scaphoid and lunate.

BRIEF DESCRIPTION OF THE DRAWINGS

It will be appreciated that the drawings are not necessarily to scale, with emphasis instead being placed on illustrating the various aspects and features of embodiments of the invention, in which.

DETAILED DESCRIPTION OF THE ILLUSTRATED EMBODIMENTS

Embodiments of the present invention are described below with reference to the above described Figures. It is, however, expressly noted that the present invention is not limited to the embodiments depicted in the Figures, but rather the intention is that modifications that are apparent to the person skilled in the art and equivalents thereof are also included.

Implant

Figure 1:
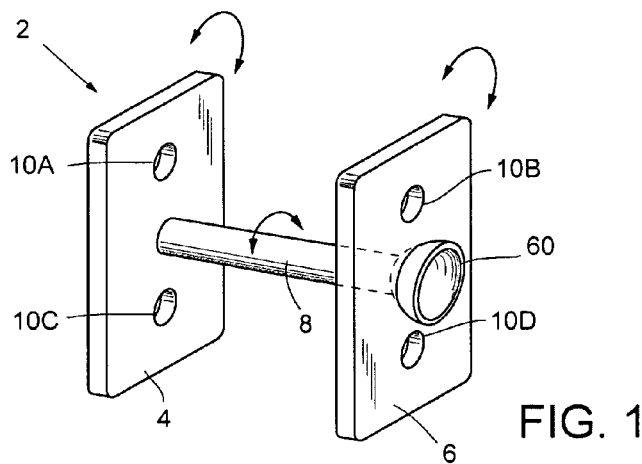
FIG. 1 is a perspective view of a preferred implant assembly.

FIG. 1 depicts a preferred implant 2 that includes first and second plates 4 and 6 that are coupled together by a lateral rod 8. The first and second plates 4 and 6 are preferably made of pyrocarbon or other turbostratic carbons to allow a superior interface with small bones. Pyrocarbon and other turbostratic carbons have the same, or similar, modulation of elasticity as the bone into which it is implanted. "Pyrocarbon," also known as pyrolytic carbon, belongs to the family of turbostratic carbons, which have a similar structure to graphite, but are more durable. In contrast to graphite, pyrocarbon and other turbostratic carbons are made of disordered layers that result in wrinkles or distortions. Pyrocarbon is advantageous with the teachings herein as it has a lesser chance of destroying and pulling out of the targeted bone compared to metals. Although highly non-preferred for the reasons mentioned above, other materials such as metals, including titanium, surgical steel, and the like, for example can also be used to construct the plates 4 and 6.

Preferred rods 8 are made from metal, and more specifically titanium. More specifically, preferred rotatable rods 8 that can be used with the teachings herein are cylindrical or substantially so, or in the shape of a rectangular parallelepiped, or substantially so. A preferred rod 8 is no longer than 1 inch in length.

Figure 3:
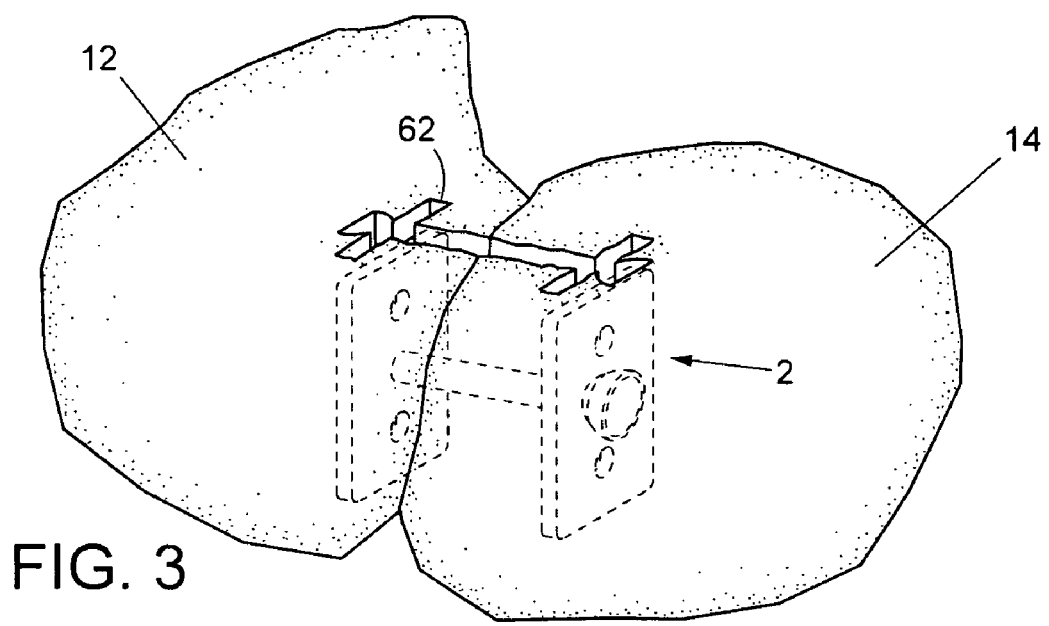
FIG. 3 is another perspective view of a preferred device implanted in the wrist of a patient in need.

Preferred plates 4 and 6 are rectangular, such that the width of the plate is inserted first into the bone (scaphoid 12 and lunate 14), and the length of the plate runs in the dorsal-volar plane, as depicted in FIG. 3. Other suitable non-preferred shapes can include polygonal forms non-exclusively including squares, triangles, and circles, for example. Preferred shapes of plates 4 and 6 are configured such that they are completely embedded within the scaphoid 12 and the lunate 14 after they are implanted, such that they not extend past the cortices of the scaphoid 12 or lunate 14. Preferred implants 2 are configured to be implanted in the scaphoid 12 and lunate 14 and can advantageously be less than a cubic inch in size.

Preferred assemblies herein include means for rotation that couple the rod 8 to the plates 4 and 6. Said means for rotation advantageously are configured to allow the rod 8 to rotate in either a forward and backward direction between the plates 4 and 6. Additionally or alternatively, said means for rotation can also allow 1 or more plates 4 and 6 to rotate in either a forward or backward direction around the rod 8. Said means for rotation can include the rod 8 having a smaller diameter or cross-section than the perimeter of the hole in the plates 4 and 6 configured to receive said rod 8. The rod 8 can be configured to not slide out of the holes in the plates 4 and 6 by including an anchor. According to further embodiments, the plates 4 and 6 are secured, or substantially so in the cut out space 62 in the bones 12 and 14 such that they are not rotating freely within the cut out space 62 but at the same time can be configured to rotate around the rod 8 as the scaphoid and lunate 12 and 14 move.

Figure 2:
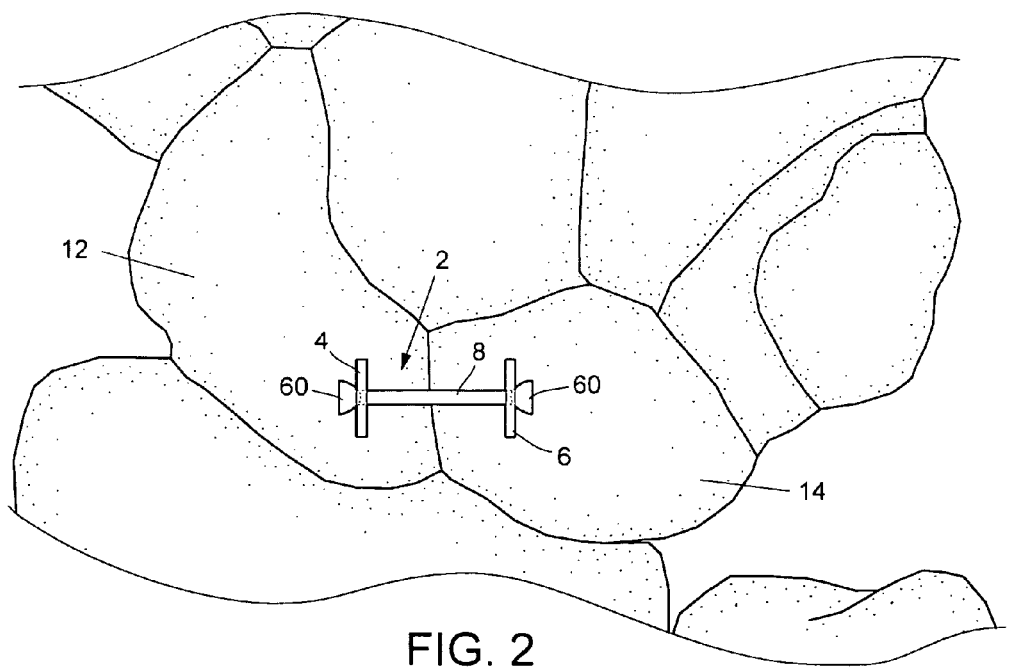
FIG. 2 is a perspective birds-eye view of an assembly implanted in the wrist of a patient in need.

As a preferred example of an anchor, the ends of the rod 8 can each include a hemisphere 60 positioned on the outer part of the plates 4 and 6, as shown in FIGS. 1, 2, 3, 5 and 7. FIG. 2 shows the preferred configuration of both hemispheres 60. Said hemispheres 60 can either be solid or hollow. Preferably the convex end of the hemisphere 60 faces toward its respective plate 4 and 6 while the concave (hollowed hemisphere) or flat portion (solid hemisphere) of the hemisphere 60 faces away from its respective plate 4 and 6. Preferred plates 4 and 6 can include recessed concaved portions configured to allow the convex faces of the hemispheres to rotate within. According to other embodiments, the faces of the plates 4 and 6 can be planar or substantially so.

The rod 8 can also be rotatably coupled to the plates 4 and 6 in numerous other ways. For example, different shapes of anchors can be used besides the hemispheres 60, including spherical, ovular, hemiovular, disc shaped anchors, and the like. The anchors can also be 1 or more pins or protrusions that project from the ends of the rod outward past the plates. Additionally, the plates 4 and 6 can include internal facing sheaths configured to rotatably hold the ends of the rod, an assembly similar to a closet rod and its end pieces. According to further embodiments, the ends of the rod can include discs or other end pieces that rotate within a hollowed out section within the plates.

Preferred assemblies hold the alignment of the scaphoid and lunate while the body incorporates the natural tissue into the scaphoid and lunate. According to preferred embodiments, the assemblies herein are not designed to replace the scapho-lunate ligament, but rather are designed to enhance the natural tissue repair. Preferred assemblies provide sufficient strength for enhancing the repair during early motion. Natural repair without the use of the assemblies herein would not be as strong as repair would be using the teachings herein. The implants 2 herein are preferably designed to supplement the strength of these tissues for the life of the patient. The patient's natural repair mechanisms combined with the implants 2 provided herein increase the strength of the repair and expand the final range of motion in the wrist.

The plates 4 and 6 preferably include perforations 10a, 10b, 10c, and 10d. These perforations can allow bone ingrowth and/or fixation by Kirschner wires 58 ("K-wires") made of carbon or an absorbable type. Perforations can also be used to pack grafts, such as bone or artificial material to enhance fusion. Other arrangements and number of perforations are also readily contemplated herein.

Method

Figure 4:
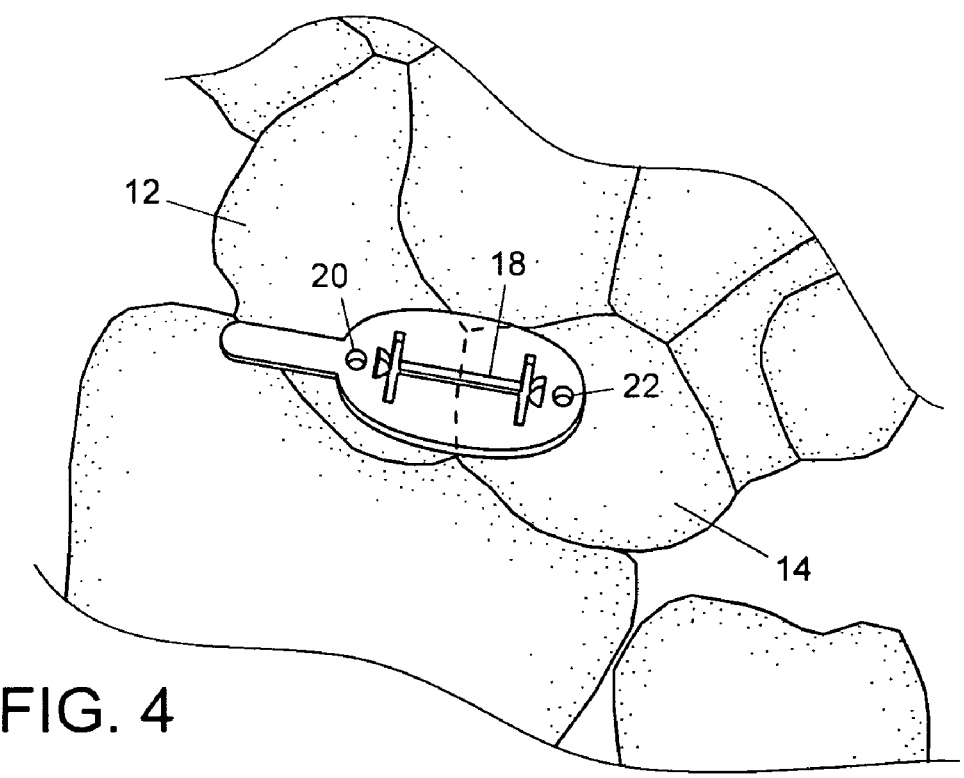
FIG. 4 is a perspective view of a cutting jig having an outline of the implanted assembly.

Reduction of the scapho-lunate gap and carpal angles should be achieved prior to insertion of the implant 2. A preferred method includes positioning a cutting jig 16 on the dorsal face of the scaphoid 12 and lunate 14 as shown in FIG. 4. The cutting jig 16 preferably includes an outline 18 of the shape of the implant 2 to guide the surgeon. Preferably the cutting jig 16 is aligned such that the outline 18 overlaps both the scaphoid 12 and lunate 14, more specifically such that the first plate 4 will be implanted into the scaphoid 12 while the second plate 6 will be implanted into the lunate 14. Different shaped outlines can be used for different shapes of implants.

According to preferred embodiments, holes 20 and 22 in the cutting jig 16 can be used along with pins or wires (e.g., K-wires) to maintain the cutting jig 16 in the correct position. Holding the cutting jig 16 this way also maintains the scapho-lunate approximation, allowing the previously placed temporary pins or wires between the scaphoid and lunate to be removed.

Means for cutting out the outline 18 in the scaphoid 12 and lunate 14 can be applied. Preferred cutting means include a micro-saggital saw or burr. A small curette can preferably facilitate bone removal outlined in the scaphoid 12 and lunate 14 to make a suitable space 62 for the implant 2. Advantageously, two different cutting instruments can be used. The longer cutting instrument can be used to cut out the space for the plates 4 and 6 while a shorter cutting instrument can be used to cut out the space for the rod 8.

Figure 5:
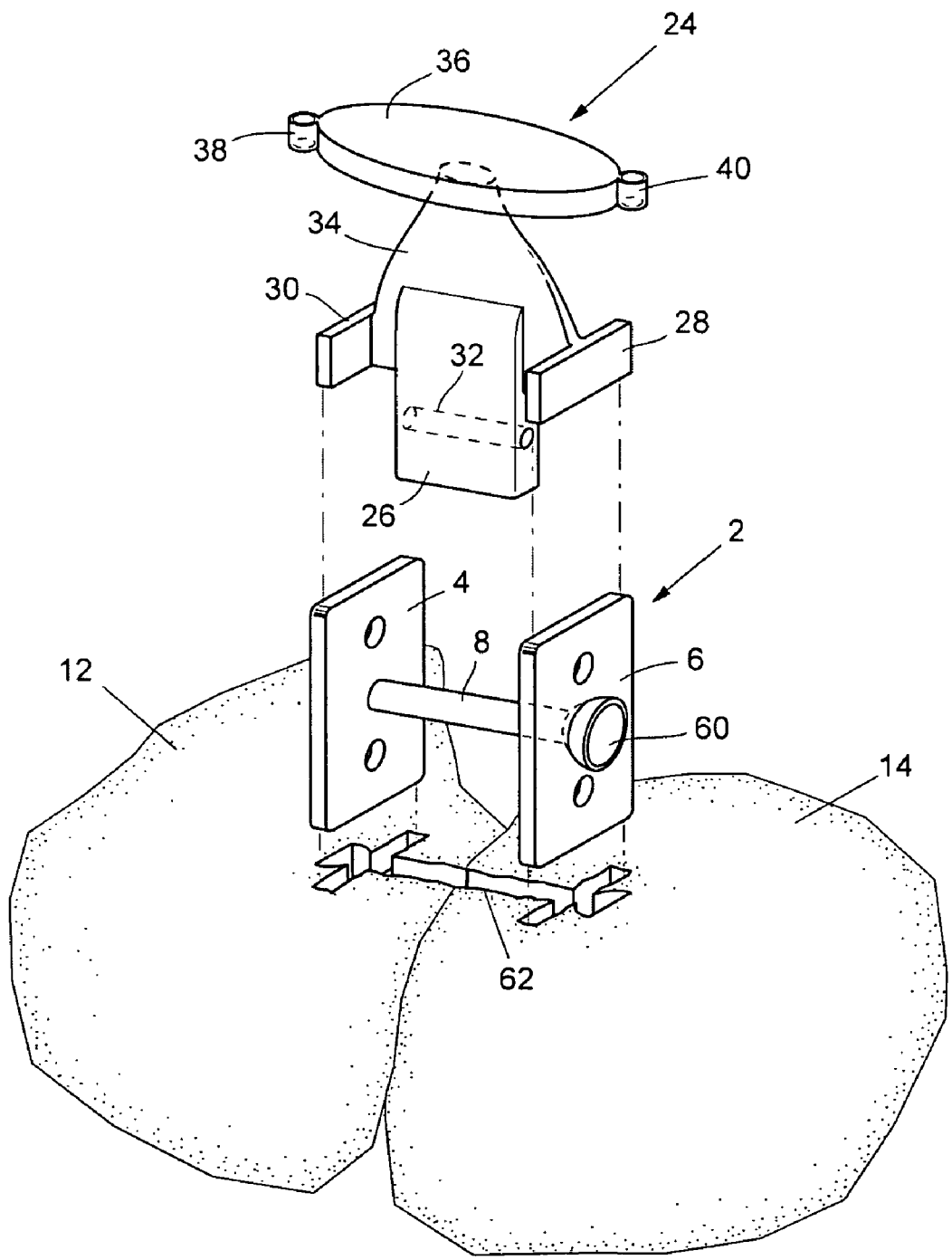
FIG. 5 is a perspective view showing an implant assembly being implanted into the wrist of a patient in need.
Figure 6:
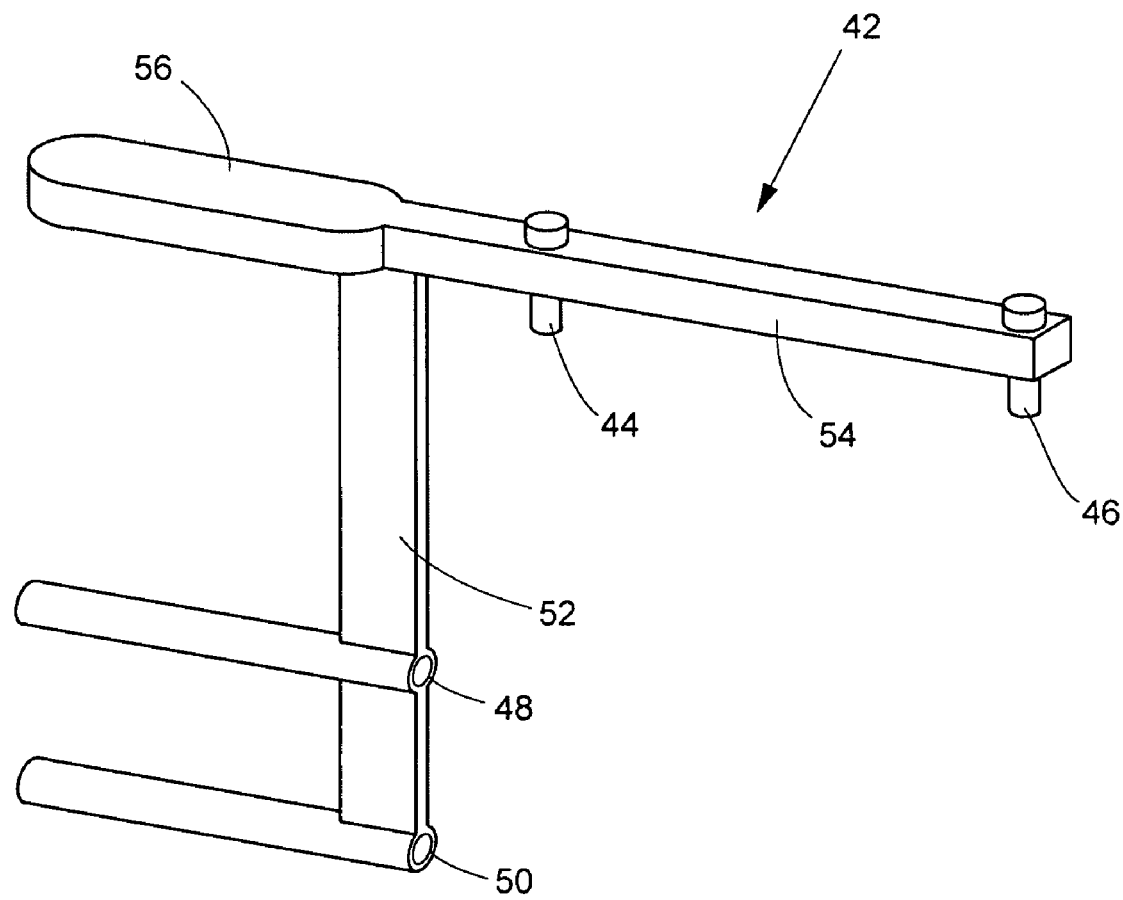
FIG. 6 is a perspective view of a K-wire jig.

After the outline 18 has been cut out, the implant 2 can be inserted into the newly created space 62 in the scaphoid 12 and the lunate 14. The implant 2 is preferably inserted in the position shown in FIG. 3, such that the shorter sides of the plates 4 and 6 are inserted downward into the scaphoid 12 and lunate 14. FIG. 5 depicts a preferred way of inserting the implant 2 into the scaphoid 12 and lunate 14. Advantageously, an impactor tamp 24 can be used. Preferred impactor tamps 24 are configured to be held by the health provider implanting the device 2 such that when sufficient force is applied, the implant 2 is pressed into the space 62 in the scaphoid 12 and lunate 14.

Preferred tamps 24 include an upper portion 36 configured to allow the user to apply force to and a lower portion 34 configured to press the device into the bones. The upper portion 36 preferably includes two sheaths 38 and 40 configured to receive pegs 44 and 46 from an alignment jig 42. The lower section preferably includes three attached members. The first member 26 is preferably configured to apply pressure to the rod 8, and a second 30 and third member 28 are preferably configured to apply pressure on the plates 4 and 6. Preferably, the first member 26 is configured to apply user generated pressure to at least half the length of the rod 8, but preferably 75% or more of the length of the rod 8. Similarly, it is preferable that the second and third members 30 and 28 are configured to apply user generated pressure to at least half the width of the plates 4 and 6, but preferably 75% or more of the width of the plates 4 and 6. Preferred tamps 24 will also include an aperture 32 configured to receive a K-wire 58, and that aligns with perforations 10a and 10b when the first member 26 is placed on top of the rod 8. Other shaped tamps or instruments for inserting the implants 2 herein can also be used.

Figure 7:
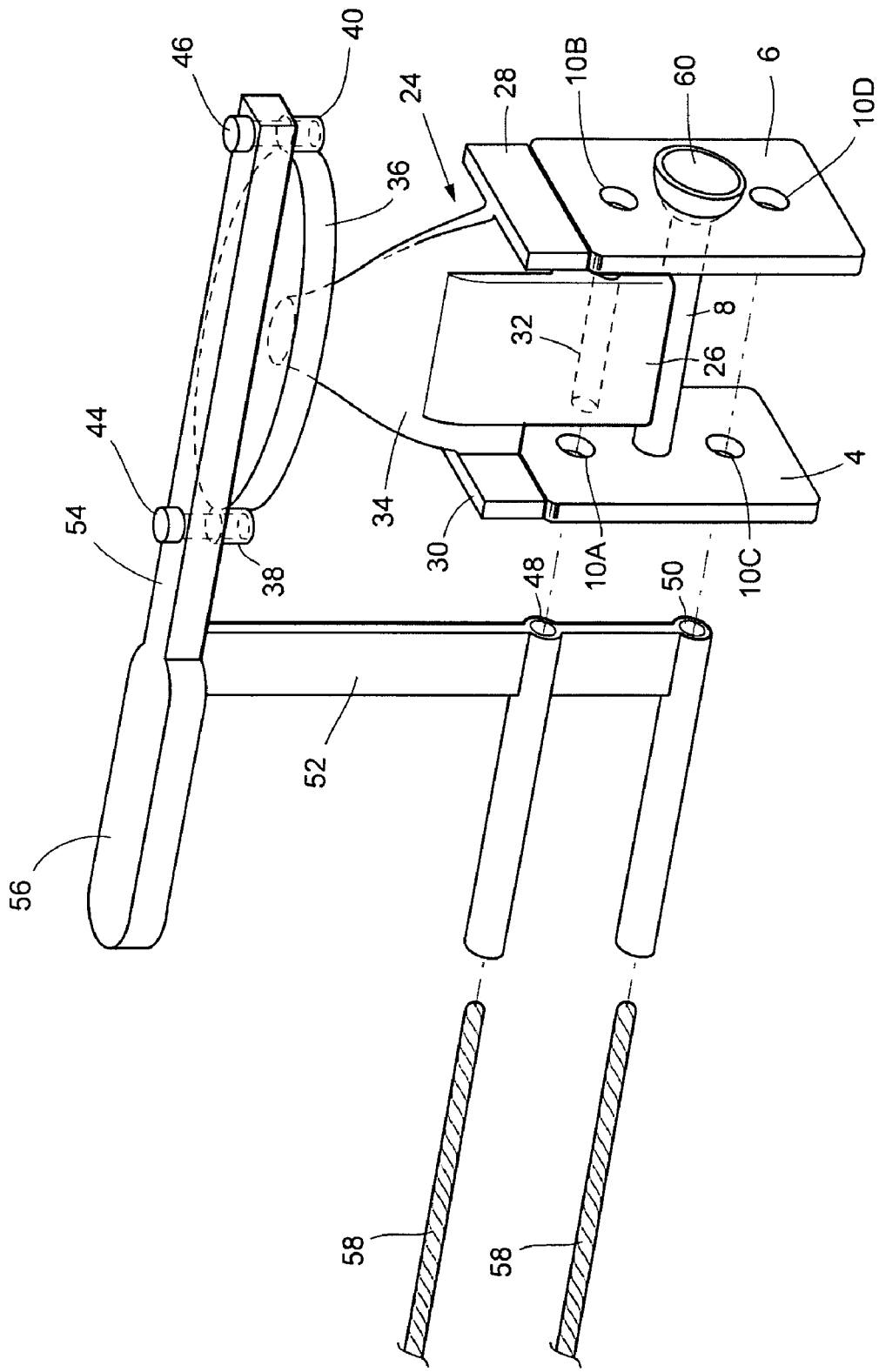
FIG. 7 is a perspective view of a K-wire jig, K-wires, tamp, and implant assembly.

Preferred tamps 24 are configured to work either alone or in conjunction with an alignment jig 42. Preferred alignment jigs 42 include a handle 56, a horizontal extension 54 that are coupled, preferably perpendicularly to a vertical extension 52. Preferably the horizontal extension 54 includes two pegs 44 and 46 configured to couple with the sheaths 38 and 40 of the tamp 24 as depicted in FIG. 7, for example. Preferred pegs 44 and 46 can be spring loaded or not.

The vertical extension 52 of the alignment jig 42 preferably includes one or more apertures 48 and 50 for receiving one or more K-wires 58. Preferably the implant 2, the tamp 24 and the alignment jig 42 can be aligned after implantation such that a K-wire 58 can pass through the first aperture 48, the first perforation 10a in the first plate 4, the aperture 32 in the tamp 24 and the second perforation 10b in the second plate 6. Likewise a second K-wire 58 can pass trough the second aperture 50, the third perforation 10c in the first plate 4, and the fourth perforation 10d in the second plate 6. Preferred apertures 48 and 50 extend away from the vertical extension 52 towards the handle 56. Advantageously, the alignment jig 42 can include adjustable means to alter the length and/or configuration of its pieces, or be configured to be used from either a radial or ulnar orientation.

K-wire alignment through the jig 42 provides enough stabilizing fixation that it allows early active motion of the wrist by the patient. Preferred K-wires 58 are approximately 4 to 8 inches in length and ranging in diameters from 0.026 to 0.062 inches although other suitable sizes can be used with the teachings herein. Preferred K-wires 58 are carbon based or otherwise bioabsorbable, such that they do not need to be removed. In other preferred embodiments, the K-wires 58 can be of metal and require later removal.

According to preferred embodiments, no permanent external or internal K-wires are required within the scaphoid 12 or lunate 14 using the teachings herein. According to more specific embodiments 1 or more temporary K-wires can be used to immobilize the scaphoid for a period of time after the surgery, usually between 6-7 weeks, more preferably at 6 weeks. Prior to removal of this scapho-capitate or scapho-lunate K-wire, protected early active motion can begin, thus decreasing scar formation, adhesions, and loss of motion.

Those with skill in the art could recognize the use of the implants and methods provided herein beyond just fixating the scaphoid and lunate bones. For example, the teachings herein could be used to fix other similar small adjacent bones in the body.

The invention may be embodied in other specific forms besides and beyond those described herein. The foregoing embodiments are therefore to be considered in all respects illustrative rather than limiting, and the scope of the invention is defined and limited only by the appended claims and their equivalents, rather than by the foregoing description.

What is claimed is:

1. A surgical kit comprising: a fixation device configured to be implanted into the scaphoid and lunate of a patient in need and comprising a first plate having inward and outward faces and configured to be implanted into the scaphoid and a second plate having inward and outward faces and configured to be implanted into the lunate, wherein said inward faces of the first and second plates are coupled together by a lateral, rotatable, rod having first and second ends individually coupled to the first and second plates, wherein said first plate comprises a first hole and the second plate comprises a second hole laterally aligned with said first hole, wherein said first and second holes comprise a larger perimeter than a cross-section of the rod, wherein the rod's first and second ends are passed through said first and second holes respectively and are individually coupled to the outward faces of the first and second plates respectively; and a cutting jig having an aperture having an outline of the entire fixation device and configured to allow a health provider to cut the shape of the fixation device into the scaphoid and lunate.

2. The surgical kit of claim 1, further comprising a tamp for implanting said fixation device.

3. The surgical kit of claim 2, further comprising a alignment jig for aligning the fixation device.

4. The surgical kit of claim 1, further comprising first and second anchors, wherein said first and second anchors are hemispheres in shape, such that the convex face of the hemisphere anchors are positioned toward the outward faces of the first and second plates.

5. The surgical kit of claim 4, wherein said outward faces of the first and second plates individually include a concave area configured to receive the convex faces of the hemisphere anchors.

6. The surgical kit of claim 1, wherein said first plate further comprises one or more perforations laterally aligned with one or more perforations on the second plate and wherein the one or more laterally aligned perforations are configured to receive a Kirschner wire.

7. The surgical kit of claim 1, wherein said first and second plates comprise pyrocarbon.

8. A surgical kit for implanting a fixation device into the scaphoid and lunate of a patient in need comprising: a fixation device having first and second plates connected by a rotatable rod having first and second end pieces, wherein said first plate is configured to be entirely implanted into the scaphoid and said second plate is configured to be entirely implanted into the lunate, wherein said first plate comprises a first hole and the second plate comprises a second hole laterally aligned with said first hole, wherein said first and second holes comprise a larger perimeter than a cross-section of the rod, wherein said rod is passed through said first and second holes such that said first and second end pieces are respectively positioned inside a hollowed out section within the first and second plates, such that the end pieces are allowed to rotate within said hollowed out section; and a cutting jig having an aperture having an outline of the entire fixation device and configured to allow a health provider to cut the shape of the fixation device into the scaphoid and lunate.

9. The surgical kit of claim 8, further comprising a tamp for implanting said fixation device.

10. The surgical kit of claim 9, further comprising a alignment jig for aligning the implant.

11. The surgical kit of claim 10, further comprising Kirschner wires for temporarily aligning said fixation device in the scaphoid and lunate.

* * * * *